US00PP09171P

United States Patent [19]

Christensen

[11] Patent Number: Plant 9,171

[45] Date of Patent: Jun. 20, 1995

[54] FLORIBUNDA ROSE PLANT NAMED JACCOFL

[75] Inventor: Jack E. Christensen, Ontario, Calif.

[73] Assignee: Bear Creek Gardens, Inc., Medford, Oreg.

[21] Appl. No.: 201,240

[22] Filed: Feb. 24, 1994

[51] Int. Cl.[6] ..... A01H 5/00

[52] U.S. Cl. ..... Plt./22

[58] Field of Search ..... Plt. 22, 24, 25

[56] References Cited

U.S. PATENT DOCUMENTS

P.P. 3,519 3/1974 Delbard ..... Plt./22

*Primary Examiner*—Howard J. Locker

*Attorney, Agent, or Firm*—Klarquist Sparkman Campbell Leigh & Whinston

[57] ABSTRACT

Rose plant of floribunda class having distinctive flower color; dark green, glossy foliage; compact but vigorous; and resistance to rust and powdery mildew.

1 Drawing Sheet

The present invention relates to a new and distinct variety of rose plant of the floribunda class which was originated by me by crossing the variety Meigronuri, U.S. Plant Pat. No. 4,625, with an unnamed seedling, the latter being the result of a cross of an unnamed seedling with the variety ARObri (U.S. Plant Pat. No. 4,659).

The primary objective of this breeding was to produce a new rose variety having the dark green foliage and good disease resistance of the female parent combined with the healthy, dark green foliage and vigor of the male parent. Both parents have yellow flowers, but the male parent has orange in its genetic background. The expected orange of some offspring is displayed in JACcofl. This objective was substantially achieved, along with other desirable improvements, as evidenced by the following unique combination of characteristics that are outstanding in the new variety and that distinguish it from its parents, as well as from all other varieties of which I am aware:

1. Unique, orange-yellow (copper) color on one side of the petals;
2. Compact but vigorous growth habit;
3. Dark green, glossy foliage; and
4. Resistance to powdery mildew and rust.

Asexual reproduction of this new variety by budding as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed descriptions of my new rose cultivar with color description using terminology in accordance with The Royal Horticultural Society (London) Colour Chart, except where ordinary dictionary significance of color is indicated.

Parentage:

*Pollen parent.*—Unknown seedling.

*Seed patent.*—Meigrounri, U.S. Plant Pat. No. 4,625.

Classification:

*Botanical.*—*Rosa hybrida.*

*Commercial.*—Floribunda.

FLOWER

Observations made from specimens grown in garden environments in Somis, Calif., from May to October, 1993.

Blooming habit: Recurrent.

Bud:

*Size.*—4 cm long when the petals start to unfurl.

*Form.*—Long; pointed ovoid.

*Color.*—When sepals first divide, and color is Yellow-Orange Group 15D. When half blown, the upper sides of the patels are Orange Group 29A (except at the petal base, where they are Yellow Group 15C) and the lower sides of the petals are Yellow-Orange Group 15D.

*Sepals.*—Color: Green Group 138C. Surface texture: Covered in fine hairs. There are three lightly appendaged sepals. There are two unappendaged sepals with hairy edges.

*Receptacle.*—Color: Green Group 139C. Shape: Funnel. Size: Small (9.5 mm×9.5 mm). Surface: Smooth.

*Peduncle.*—Length: Medium (76 to 80 mm). Surface: Smooth. Color: Medium green. Strength: Stiff, erect.

Bloom:

*Size.*—Large. Average open size is 80 mm in diameter.

Borne.—Singly and several together in rounded clusters of 3 to 5 flowers.

*Stems.*—Medium (36 to 41 cm), strong.

*Form.*—When first open: High centered. Permanence: Flattens, outer petals curl back.

*Petalage.*—Number of petals under normal conditions: 40.

*Color.*—The upper, outer side of the petals is Orange Group 29A, with Yellow-Orange Group 15C on the lower part of each petal. The major color on the upper side is Orange Group 29A. The reverse side and base of the petals is Yellow-Orange Group 15D.

*Variegations.*—None.

*Discoloration.*—The general tonality at the end of the first day: No change. At the end of the third day, very little change. However, by day 4 or 5 under bright sunlight, the color will fade to Orange Group 29C.

*Fragrance.*—Slight.

Petals:

*Texture.*—Thick.

*Shape.*—Round to deltoid.

*Form.*—Tips are slightly recurved.

*Arrangement.*—Imbricated, with few petaloids in the center.

*Persistence.*—Hang on and dry.

*Lastingness.*—On the plant: Long (7 to 8 days). As a cut flower: Long (8 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Reddish at top, becoming pink, then white at the base.

*Stigmas.*—Color: Greenish white.

Form: Bush.

Growth: Vigorous; upright; branching; average height in California of 1 to 1.4 meters with average width of 90 cm.

Foliage:

*Number of leaflets on normal mid-stem leaves.*—5 to 7.

*Size.*—Large (15 cm×10 cm).

*Quantity.*—Normal.

*Color.*—New Foliage: Reddish Greyed Red Group 180B). Old foliage: Dark green (Green Group 139A).

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, serrated.

*Disease resistance.*—Resistant to mildew and rust under normal growing conditions at Somis, Calif.

Wood:

*New wood.*—Color: Light green. Bark: Smooth.

*Old Wood.*—Color: Green. Bark: Smooth.

Prickles:

*Quantity.*—Ordinary on main canes from base. Ordinary on laterals from main canes.

*Form.*—Short, hooked slightly downward.

*Color when young.*—Green and red.

Small prickles:

*Quantity.*—None on main stalks. None on laterals.

I claim:

1. A new and distinct variety of rose plant of the floribunda class, substantially as herein shown and described, characterized particularly as to novelty by its distinctive flower color; dark green, glossy foliage; compact but vigorous growth; and resistance to rust and powdery mildew.

* * * * *

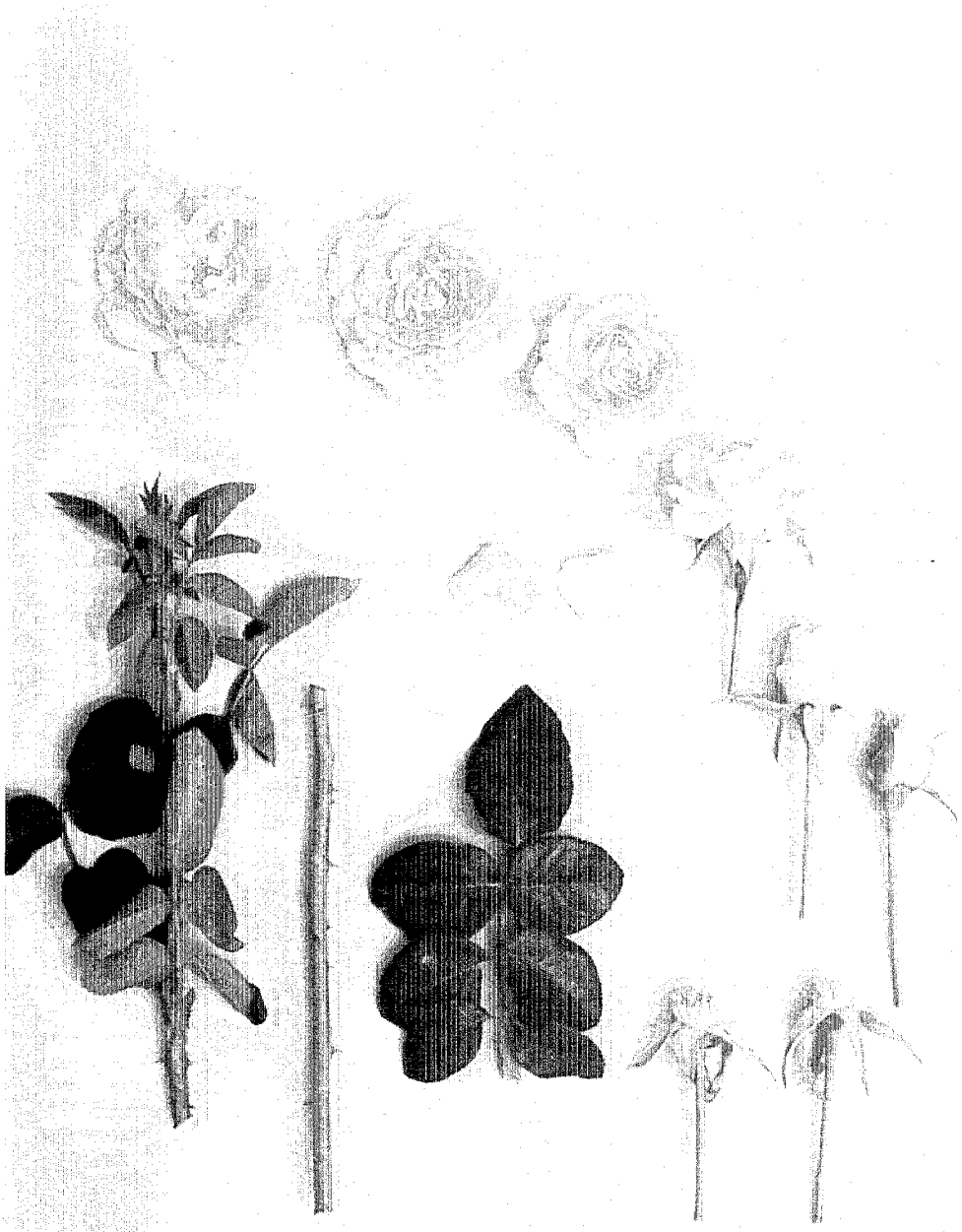
JAC cofl

UNITED STATES PATENT AND TRADEMARK OFFICE

CERTIFICATE OF CORRECTION

PATENT NO. : Plant 9,171
DATED : June 20, 1995
INVENTOR(S) : Jack E. Christensen It is certified that error appears in the above-indentified patent and that said Letters Patent is hereby corrected as shown below:

Title page, item [57],

Line 2: "vigorous;" should be --vigorous growth;--

Column 2, line 12: "and color" should be --bud color--

Column 2, line 14: "patels" should be --petals--

Signed and Sealed this
Eighth Day of July, 1997

Bruce Lehman

*Attest:*

BRUCE LEHMAN

*Attesting Officer*

*Commissioner of Patents and Trademarks*